(12) United States Patent
Kirsch

(10) Patent No.: US 11,045,185 B2
(45) Date of Patent: Jun. 29, 2021

(54) KNOTLESS ENDOSTITCH SUTURE RETAINER

(71) Applicant: Covidien LP, Mansfield, MA (US)

(72) Inventor: David Kirsch, Madison, CT (US)

(73) Assignee: Covidien LP, Mansfield, MA (US)

( * ) Notice: Subject to any disclaimer, the term of this patent is extended or adjusted under 35 U.S.C. 154(b) by 245 days.

(21) Appl. No.: 15/920,633

(22) Filed: Mar. 14, 2018

(65) Prior Publication Data

US 2018/0199933 A1   Jul. 19, 2018

Related U.S. Application Data

(62) Division of application No. 12/726,434, filed on Mar. 18, 2010, now Pat. No. 9,943,306.

(60) Provisional application No. 61/169,026, filed on Apr. 14, 2009.

(51) Int. Cl.
| | | |
|---|---|---|
| A61B 17/04 | (2006.01) | |
| A61B 17/06 | (2006.01) | |
| A61B 17/062 | (2006.01) | |

(52) U.S. Cl.
CPC ...... *A61B 17/0469* (2013.01); *A61B 17/0625* (2013.01); *A61B 17/06133* (2013.01); *A61B 2017/0479* (2013.01); *A61B 2017/06142* (2013.01)

(58) Field of Classification Search
None
See application file for complete search history.

(56) References Cited

U.S. PATENT DOCUMENTS

| 2,012,776 A | 8/1935 | Roeder |
| 2,692,676 A | 10/1954 | Grover |
| 3,106,417 A | 10/1963 | Clow |
| 3,521,918 A | 7/1970 | Hammond |
| 3,580,256 A | 5/1971 | Wilkinson |
| 3,752,516 A | 8/1973 | Mumma |
| 4,120,395 A | 10/1978 | Mandel |
| 4,711,476 A | 12/1987 | Hanson |
| 5,350,060 A | 9/1994 | Alpern et al. |

(Continued)

FOREIGN PATENT DOCUMENTS

| EP | 0055823 A1 | 7/1982 |
| EP | 0726062 A2 | 8/1996 |

(Continued)

OTHER PUBLICATIONS

European Search Report for EP 10250763.9-1269 dated Jun. 28, 2010 (3 pages).

(Continued)

*Primary Examiner* — Shaun L David
(74) *Attorney, Agent, or Firm* — Carter DeLuca & Farrell LLP

(57) ABSTRACT

A suture retainer is provided for supplying a surgical needle and an associated length of relatively stiff suture material to a surgical suturing apparatus. The suture retainer generally includes a body portion defining a suture tray and a loading unit positioned on the body portion. The loading unit is provided to retain a surgical needle in a position to be grasped by a surgical suturing apparatus. The suture tray retains the length of relatively stiff suture in a manner which prevents the relatively stiff suture from bending or otherwise being deformed.

18 Claims, 12 Drawing Sheets

(56) References Cited

U.S. PATENT DOCUMENTS

| | | |
|---|---|---|
| 5,358,498 A | 10/1994 | Shave |
| 5,389,103 A | 2/1995 | Melzer et al. |
| 5,391,176 A | 2/1995 | de la Torre |
| 5,405,352 A | 4/1995 | Weston |
| 5,472,446 A | 12/1995 | de la Torre |
| 5,478,344 A | 12/1995 | Stone et al. |
| 5,478,345 A | 12/1995 | Stone et al. |
| 5,480,406 A | 1/1996 | Nolan et al. |
| 5,527,323 A | 6/1996 | Jervis et al. |
| 5,540,703 A | 7/1996 | Barker, Jr. et al. |
| 5,562,686 A | 10/1996 | Sauer et al. |
| 5,566,822 A | 10/1996 | Scanlon |
| 5,569,301 A | 10/1996 | Granger et al. |
| 5,571,090 A | 11/1996 | Sherts |
| 5,573,286 A | 11/1996 | Rogozinski |
| 5,591,181 A | 1/1997 | Stone et al. |
| 5,601,185 A | 2/1997 | Behring |
| 5,628,756 A | 5/1997 | Barker, Jr. et al. |
| 5,630,825 A | 5/1997 | de la Torre et al. |
| 5,632,751 A | 5/1997 | Piraka |
| 5,643,293 A | 7/1997 | Kogasaka et al. |
| 5,669,490 A | 9/1997 | Colligan et al. |
| 5,674,229 A | 10/1997 | Tovey et al. |
| 5,674,230 A | 10/1997 | Tovey et al. |
| 5,681,331 A | 10/1997 | de la Torre et al. |
| 5,715,942 A | 2/1998 | Li et al. |
| 5,728,107 A | 3/1998 | Zlock et al. |
| 5,728,109 A | 3/1998 | Schulze et al. |
| 5,730,747 A | 3/1998 | Ek et al. |
| 5,733,293 A | 3/1998 | Scirica et al. |
| 5,749,898 A | 5/1998 | Schulze et al. |
| 5,755,729 A | 5/1998 | de la Torre et al. |
| 5,792,153 A | 8/1998 | Swain et al. |
| 5,797,928 A | 8/1998 | Kogasaka |
| 5,814,054 A | 9/1998 | Kortenbach et al. |
| 5,814,069 A | 9/1998 | Schulze et al. |
| 5,865,836 A | 2/1999 | Miller |
| 5,871,488 A | 2/1999 | Tovey et al. |
| 5,893,592 A | 4/1999 | Schulze et al. |
| 5,894,921 A | 4/1999 | Le et al. |
| 5,908,428 A | 6/1999 | Scirica et al. |
| 5,941,430 A | 8/1999 | Kuwabara |
| 6,016,905 A | 1/2000 | Gemma et al. |
| 6,056,771 A | 5/2000 | Proto |
| 6,126,666 A | 10/2000 | Trapp et al. |
| 6,138,440 A * | 10/2000 | Gemma ............ A61B 17/06133 206/63.3 |
| 6,277,132 B1 | 8/2001 | Brhel |
| 6,533,796 B1 | 3/2003 | Sauer et al. |
| 6,596,015 B1 | 7/2003 | Pitt et al. |
| 6,719,765 B2 | 4/2004 | Bonutti |
| 6,991,635 B2 | 1/2006 | Takamoto et al. |
| 7,063,710 B2 | 6/2006 | Takamoto et al. |
| 7,191,900 B2 | 3/2007 | Opie et al. |
| 7,192,437 B2 | 3/2007 | Shalaby |
| 7,211,093 B2 | 5/2007 | Sauer et al. |
| 7,218,972 B2 | 5/2007 | Rodriguez |
| 7,232,448 B2 | 6/2007 | Battles et al. |
| 7,244,260 B2 | 7/2007 | Koseki |
| 7,309,346 B2 | 12/2007 | Martinek |
| 7,468,068 B2 | 12/2008 | Kolster |
| 7,601,164 B2 | 10/2009 | Wu |
| 9,943,306 B2 | 4/2018 | Kirsch |
| 2003/0195529 A1 | 10/2003 | Takamoto et al. |
| 2005/0154402 A1 | 7/2005 | Sauer et al. |
| 2005/0154403 A1 | 7/2005 | Sauer et al. |
| 2008/0140118 A1 | 6/2008 | Martinek |
| 2009/0138029 A1 | 5/2009 | Saliman et al. |
| 2009/0248046 A1 | 10/2009 | Primavera et al. |
| 2009/0259233 A1 | 10/2009 | Bogart et al. |
| 2010/0307934 A1 | 12/2010 | Chowaniec et al. |
| 2011/0042244 A1 | 2/2011 | Kirsch |

FOREIGN PATENT DOCUMENTS

| | | |
|---|---|---|
| EP | 2113205 A2 | 11/2009 |
| JP | H0866404 A | 3/1996 |
| JP | H11299797 A | 11/1999 |
| JP | 2006036227 A | 2/2006 |
| WO | 9722300 A1 | 6/1997 |
| WO | 9853745 A1 | 12/1998 |
| WO | 2008045333 A2 | 4/2008 |
| WO | 2008045353 A2 | 4/2008 |
| WO | 2008045355 A2 | 4/2008 |
| WO | 2008045361 A2 | 4/2008 |
| WO | 2008045367 A2 | 4/2008 |
| WO | 2008045385 A2 | 4/2008 |
| WO | 2008045386 A2 | 4/2008 |
| WO | 2008045394 A2 | 4/2008 |

OTHER PUBLICATIONS

European Office Action corresponding to EP 10 250 763.9 dated Jul. 24, 2015; 5 pp.

Canadian Office Action dated Mar. 1, 2016 in corresponding Canadian Patent Application No. 2,699,141.

Japanese Office Action issued in Japanese Patent Application No. 2010-091735, dated Dec. 4, 2013.

* cited by examiner

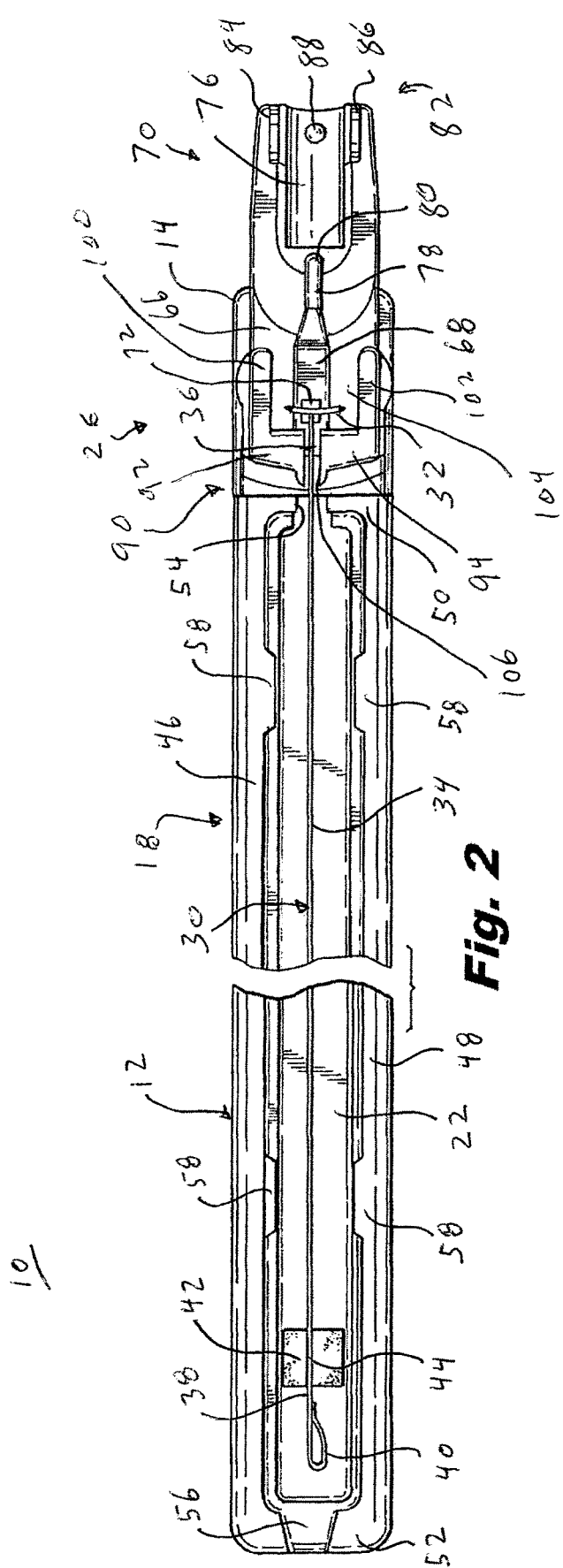
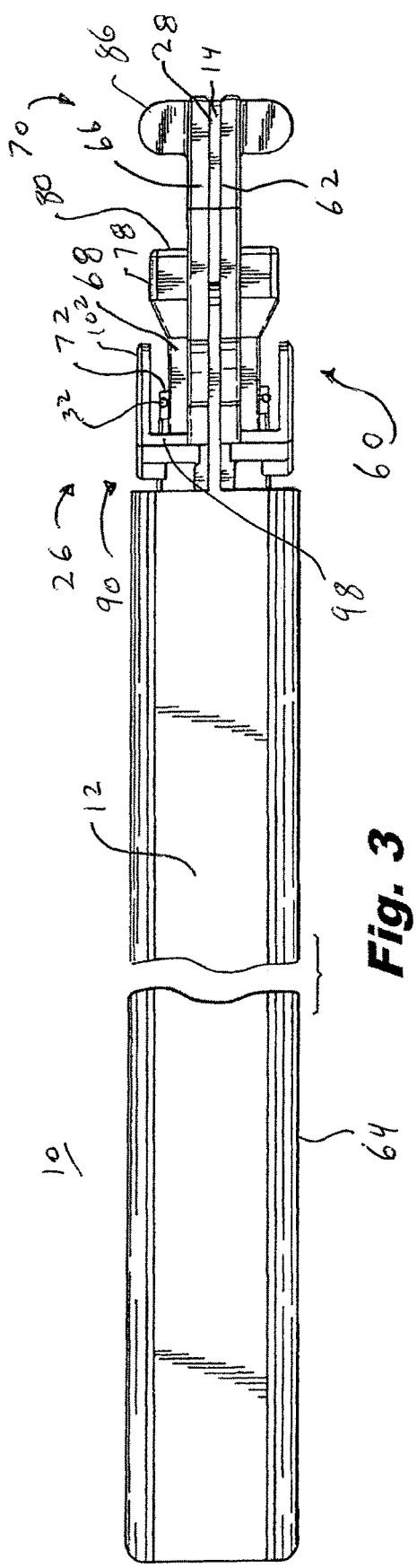
Fig. 2
Fig. 3

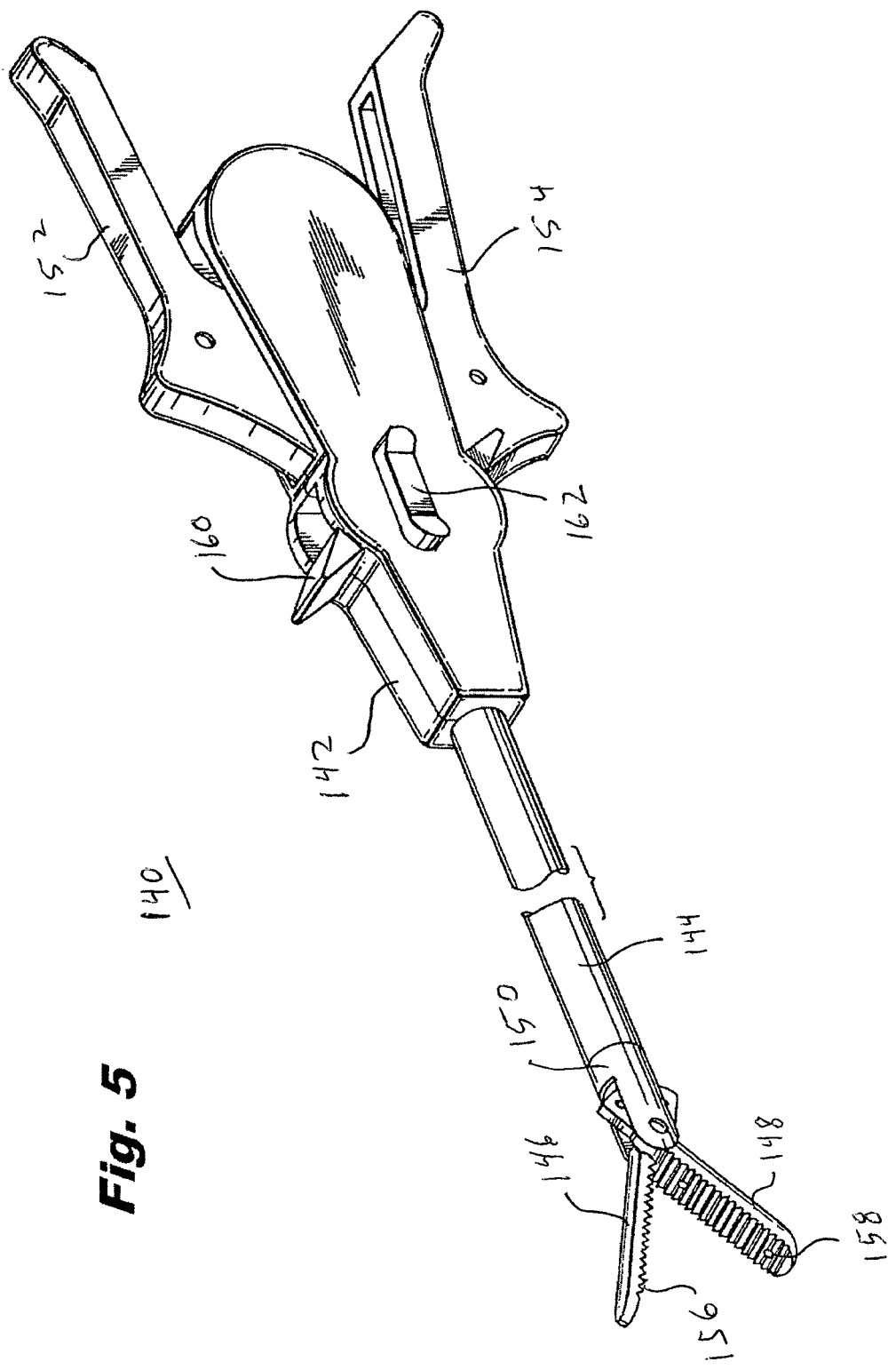

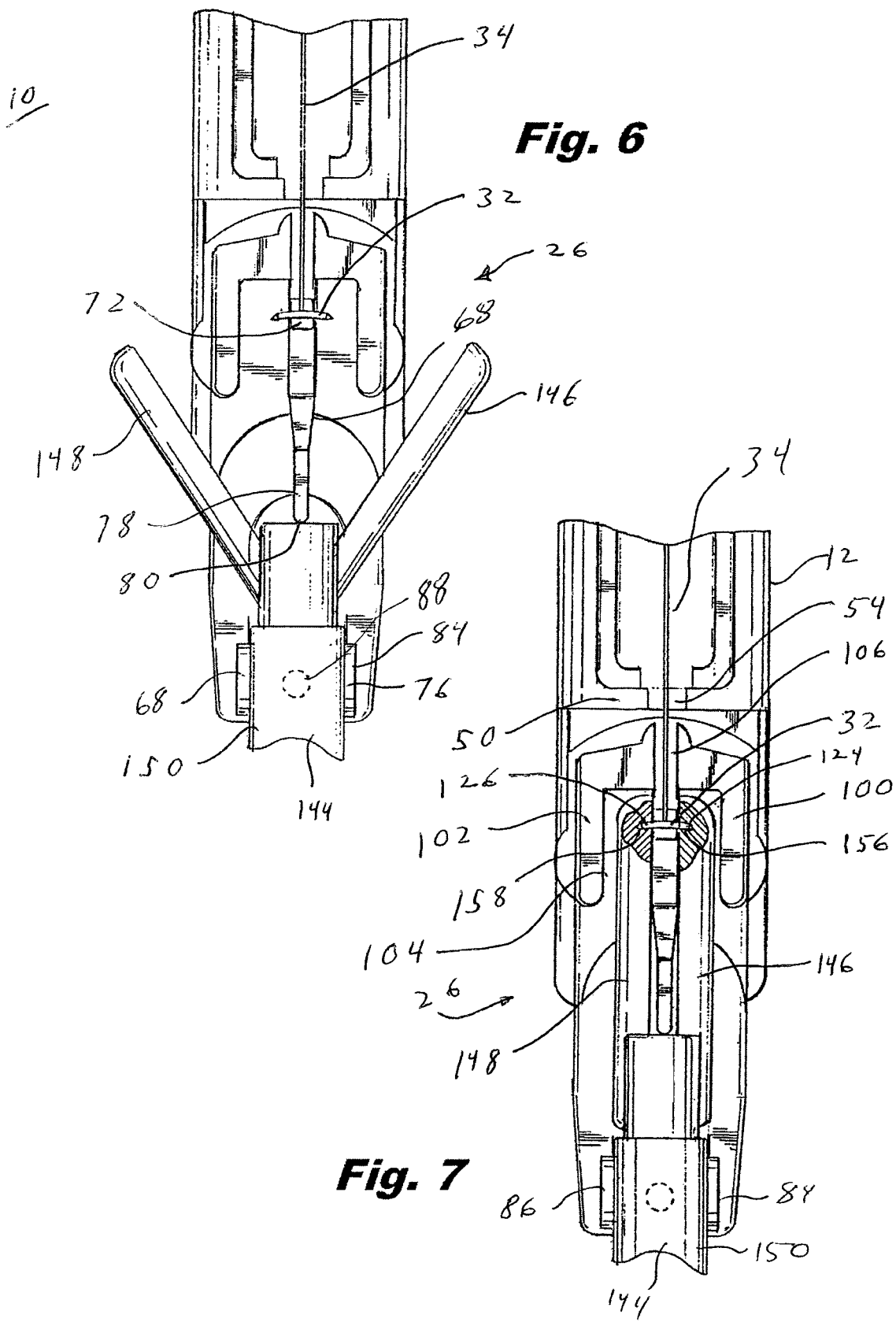

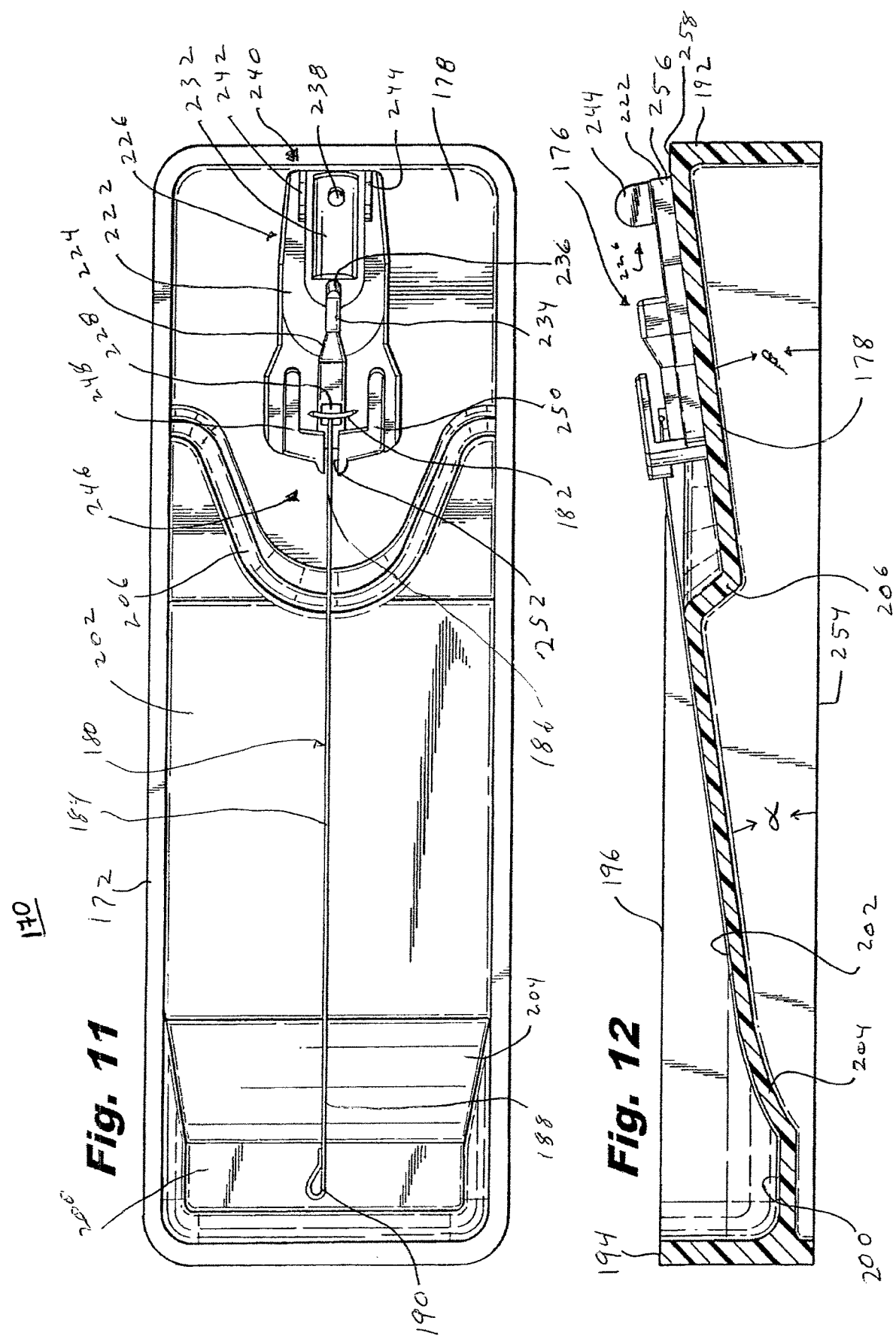

KNOTLESS ENDOSTITCH SUTURE RETAINER

CROSS-REFERENCE TO RELATED APPLICATION

This application is a Divisional of U.S. patent application Ser. No. 12/726,434 filed Mar. 18, 2010, which claims the benefit of and priority to U.S. Provisional Application Ser. No. 61/169,026, filed on Apr. 14, 2009, and the disclosures of each of the above-identified applications are hereby incorporated by reference in their entirety.

BACKGROUND

1. Technical Field

The present disclosure relates to a suture retainer for use with a knotless suture, which in embodiments, may be a barbed suture. More particularly, the present disclosure relates to a suture retainer for supplying a knotless suture and an associated surgical needle to a surgical suturing apparatus.

2. Background of Related Art

During various surgical procedures is often necessary to manipulate a surgical needle, having a length of suture material attached thereto, with a surgical suturing apparatus. This is particularly true in minimally invasive surgical procedures wherein the surgery is performed through a small incision or port allowing access to a body cavity.

Various forms of packaging or devices have been developed to provide the surgical needle and an associated length of suture material to the surgical suturing apparatus. These packages or devices typically hold the surgical needle loosely within the packaging and bend or wrap the length of suture material within the packaging to conserve space.

In a particular application, a double ended surgical needle is used in conjunction with the surgical suturing apparatus. The double ended surgical needle is alternately secured within the jaws of the surgical suturing apparatus, specifically within small holes formed within the jaws. In order to load the surgical needle within the jaws of the suturing apparatus, the jaws of the suturing apparatus and, specifically, the holes formed therein, must be precisely aligned over opposite ends of the double ended surgical needle.

Additionally, some surgical procedures are best performed with the use of a relatively stiff, barbed length of suture material having a loop at one end thereof. After suturing the appropriate tissue, the surgical needle is passed through the loop such that the barbs in the length of suture material engage the interior of the loop to lock the suture in place about the tissue. Due to the nature of the relatively stiff suture material, and the presence of barbs which tend to engage each other, it is often not possible to bend or wrap a length of suture material within compact packaging.

Therefore, a need exists for a suture retainer which is capable of precisely positioning a surgical needle for receipt by a surgical suturing apparatus and, at the same time, accommodating a relatively stiff, barbed length of suture material. Additionally, it is further desirable, to provide a suture retainer capable of supplying one or more needle suture combinations to the surgical suturing apparatus.

SUMMARY

There is disclosed a suture retainer for use with a suture assembly including a surgical needle and a length of relatively stiff suture material affixed to the surgical needle. The suture retainer generally includes an elongate body portion defining at least one suture tray and a loading unit located on the elongate body portion. The at least one suture tray supports a length of relatively stiff suture material and the loading unit supports the surgical needle affixed to the length of relatively stiff suture material. The loading unit includes a needle support member for releasably retaining the surgical needle. The loading unit is located proximal to the at least one suture tray. The elongate body portion includes a distal wall, a proximal wall, and side walls extending between the distal and proximal side walls.

In one embodiment, the proximal wall includes a gap for passage of the length of suture material between the loading unit and the suture tray.

A retainer block is positioned within the suture tray. The retainer block releasably secures a portion of the length of suture material within the suture tray. The retainer block includes a slit to frictionally receive the length of suture material.

In one embodiment, the retainer block is formed from a resilient material. In one specific embodiment, the retainer block is formed from a foam material. In an alternative specific embodiment, the retainer block is formed from a rubber material.

In a particular embodiment of the disclosed suture retainers, the elongate body portion includes a first side and a second side, each of the first and second sides including a suture tray and a loading unit.

There is also disclosed a suture retainer including an elongate body portion defining a suture tray for support of a length of relatively stiff suture material. The suture tray has a proximal tray portion, a proximal wall, a distal wall and first and second side walls extending between the proximal wall and the distal wall. The suture retainer further includes a loading unit positioned within the proximal tray portion. The suture tray includes a distal tray portion and a center tray portion intermediate the distal tray portion and the proximal tray portion.

In one embodiment, the distal tray portion is oriented substantially perpendicular to the distal wall. The center tray portion forms and angle α relative to a bottom surface of the elongate body portion. The proximal tray portion forms and angle β relative to the bottom surface of the elongate body portion.

In one embodiment, the loading unit has a base flush with an upper surface of the proximal wall.

DESCRIPTION OF THE DRAWINGS

Various embodiments of the presently disclosed knotless suture retainer are disclosed herein with reference to the drawings, wherein:

FIG. 2 is a top plan view of the knotless suture retainer;

FIG. 3 is a side view of the knotless suture retainer;

FIG. 5 is a perspective view of a surgical suturing apparatus for use with the knotless suture retainer;

FIG. 6 is a partial top view illustrating the positioning of the surgical suturing apparatus in a loading unit of the knotless suture retainer;

FIG. 7 is a view similar to FIG. 6 with jaws of the surgical suturing apparatus closed about a surgical needle held in the loading unit;

FIG. 11 is top view of the knotless suture retainer of FIG. 9;

FIG. 12 is a side view of the knotless suture retainer of FIG. 9;

DETAILED DESCRIPTION OF EMBODIMENTS

Embodiments of the presently disclosed knotless suture retainer will now be described in detail with reference to the drawings wherein like numerals designate identical or corresponding elements in each of the several views. As is common in the art, the term 'proximal" refers to that part or component closer to the user, while the term "distal" refers to that part or component further away from the user.

Figure 1:
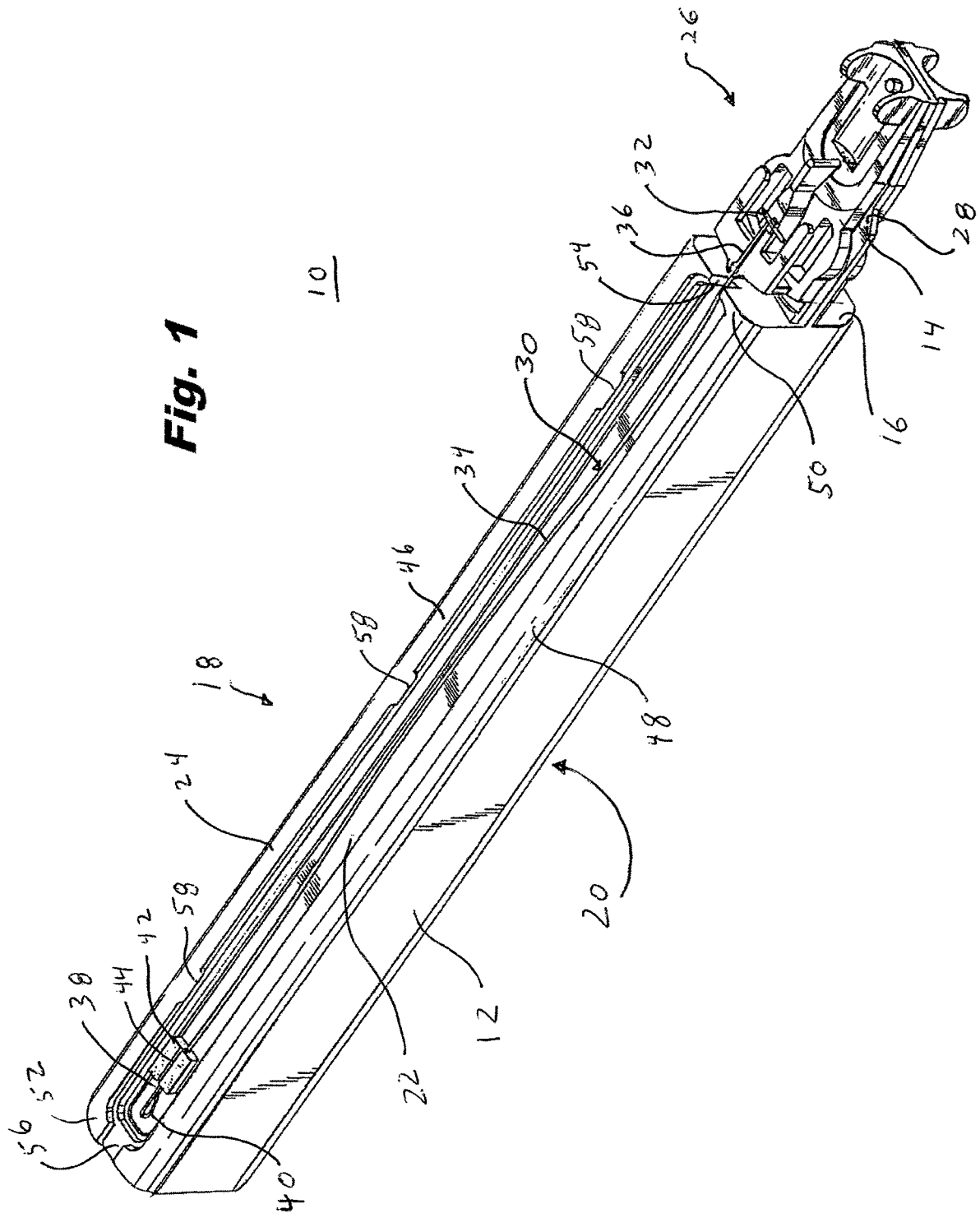
FIG. 1 is a perspective view of one embodiment of a knotless suture retainer.

Referring to FIG. 1, there is illustrated a double sided, knotless suture retainer or suture retainer 10. Suture retainer 10 includes a generally rectangular, elongate body portion 12 having a planar tongue 14 extending proximally from a proximal end 16 of elongate body portion 12. As noted herein above, suture retainer 10 is double-sided and includes a first or upper side 18 and a second or lower side 20. Upper and lower sides 18 and 20 are mirror images of each other including identical structure which function in an identical manner.

A channel or suture tray 22 is formed in a first side 24 of elongate body portion 12. A first loading unit 26 is provided on a first side 28 of planar tongue 14. As used herein, the term "suture tray" refers to an elongate holder capable of supporting a relatively stiff length of suture material without substantial bending of the suture material. Suture tray 22 and first loading unit 26 are provided to secure a suture assembly such as, for example, first suture assembly 30 within upper side 18 of elongate body portion 12. First suture assembly 30 generally includes a double-sided, surgical needle 32 which is retained within first loading unit 26. First suture assembly 30 additionally includes a length of suture material 34 having a proximal end 36 which is secured to surgical needle 32. A distal end 38 of length of suture material 34 includes a suture loop 40.

First suture assembly 30 is configured to be self-locking. Specifically, length of suture material 34 is formed of a barbed material such that when surgical needle 32 is passed through suture loop 40, the barbs (not shown) of suture material 34 may engage suture loop 40 to secure suture material 34 within suture loop 40.

Referring now to FIGS. 1 and 2, suture retainer 10 includes a first retainer, or first block 42, positioned within first suture tray 22. First block 42 includes a center slit 44 to frictionally engage distal end 38 of length of suture material 34 to secure length of suture 34 within first suture tray 22. First block 42 is formed of a resilient material, such as, for example, foam, rubber, etc.

As shown, first suture tray 22 is defined by a first sidewall 46, a second sidewall 48, a proximal end wall 50 and a distal end wall 52 formed in upper side 18 of elongate body portion 12. A proximal notch 54 is provided in proximal wall 50 to allow length of suture material 34 to pass from within first suture tray 22 and extend toward needle 32 held within first loading unit 26. A distal notch 56 may be provided in distal wall 52 to facilitate removal of a suture cover (not shown) provided over first suture tray 22. A plurality of tabs 58 may be provided in first and second side walls 46 and 48 to retain the suture cover on elongate body portion 12.

Referring for the moment to FIG. 3, and as noted herein above, suture retainer 10 is double-sided and includes a second loading unit 60 provided on a second side 62 of planar tongue 14. While not specifically shown, a second tray is formed in a second side 64 of elongate body portion 12. It should be noted that the second tray and second loading unit 60 are substantially identical to first suture tray 22 and first loading unit 26 described herein.

Figure 4:
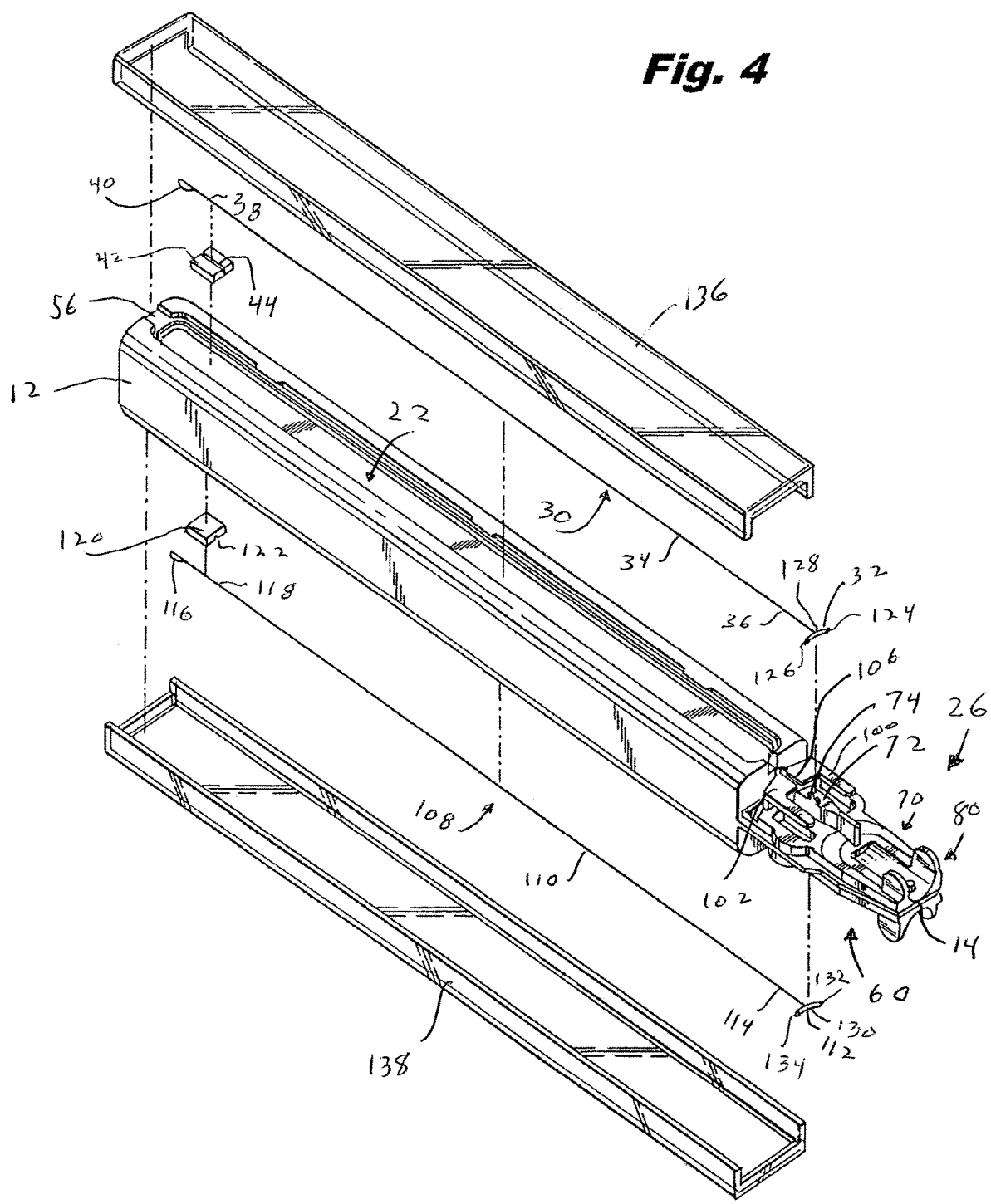
FIG. 4 is a perspective view, with parts separated, of the knotless suture retainer.

Referring now to FIGS. 2-4, the details of first loading unit 26 will now be described. As noted here in above, first loading unit 26 is provided to support and supply double ended needle 32 to a surgical suturing apparatus. First loading unit 26 includes a base 66 which may be affixed to first side 28 of planar tongue 14 or may be formed integrally with first side 28. A needle support member 68 extends vertically upwardly from base 66 and is configured to support surgical needle 32 in an elevated position relative to base 66. This allows room for jaws of a surgical suturing apparatus (not shown) to be moved into engagement with surgical needle 32. Apparatus receiving structure 70 is provided on first loading unit 26 to properly position the surgical suturing apparatus with respect to surgical needle 32.

A needle block 72 is provided on needle support member 68 to frictionally hold surgical needle 32 on needle support member 68. As best shown in FIG. 4, needle block 72 includes a needle notch 74 for receipt of surgical needle 32.

With specific reference to FIG. 2, a recess 76 is provided in base 66 for receipt of a distal end of the surgical suturing apparatus. A proximal end 78 of needle support member 68 forms an abutment surface 80 to limit the advancement of the surgical suturing apparatus within first loading unit 26. Apparatus alignment structure 82 is additionally provided to guide surgical suturing apparatus within first loading unit 26 and generally includes a pair of first and second side tabs 84 and 86 which are configured to align an elongate member of the surgical suturing apparatus properly relative to surgical needle 32. A support stud 88 is additionally provided within recess 76 and is configured to engage a recess formed within the elongate member of the surgical suturing apparatus.

Referring now to FIGS. 2 and 3, in order to guide the jaws of the surgical suturing apparatus into engagement with surgical needle 32 and prevent removal of surgical needle 32 until it has been fully grasped by the jaws of the surgical suturing instrument, first loading unit 26 is provided with blocking structure 90. Blocking structure 90 generally includes a first blocking member 92 and a second blocking member 94 extending from base 66 adjacent needle support member 68. First and second blocking members 92 and 94 include respective vertical supports 96 and 98 and L-shaped proximally extending arms 100 and 102 located above surgical needle 32. By positioning proximally extending arms 100 and 102 above surgical needle 32 room is provided for the jaws of the surgical instrument to pass under proximally extending arms 100 and 102 to surround and grasp surgical needle 32 in a manner described in more detail hereinbelow.

It should be noted herein, that first and second blocking members 92 and 94 and, specifically, proximally extending arms 100 and 102 prevent removal or lifting of surgical needle 32 from needle support member 68 until such time as surgical needle 32 has been properly grasped by the surgical suturing instrument and the jaws of the surgical suturing instrument are in a fully closed position. First and second proximally extending arms 100 and 102 defining a proximal gap 104 there between which allows the fully closed the jaws of the surgical suturing instrument to be lifted vertically to thereby remove surgical needle 32 from needle block 72. Likewise, a distal gap 106 is formed between first and second proximally extending arms 100 and 102 for passage of length of suture material 34. Distal gap 106 is in alignment with proximal notch 54 formed in elongate body portion 12.

Referring now to FIG. 4, suture retainer 10 includes a second suture assembly 108 which is positioned within a second suture tray (not shown) formed in second or lower side 20 of elongate body portion 12. Second suture assembly 108 includes a length of suture material 110 having a double ended surgical needle 112 affixed to a proximal end 114 of length of suture material 110. Length of suture material 110 is substantially identical to that described herein above including a barbed outer surface and being formed of a relatively rigid material. A suture loop 116 is formed at a distal end 118 of length of suture material 110. Upon passage of surgical needle 112 through suture loop 116, length of suture material 110 is self locking upon itself.

Suture retainer 10 additionally includes a second retainer or second block 120 having a slit 122 therein for receipt of proximal end 118 of length of suture material 110 to secure length of suture material 110 within the second tray (not shown).

As shown, double ended surgical needle 32 includes a pair of tissue penetrating tips 124 and 126. Proximal end 36 of length of suture material 30 is affixed to a center portion 128 of surgical needle 32. Likewise, a proximal end 114 of length of suture material 110 is affixed to a center portion 130 of double ended surgical needle 112. Double ended surgical needle 112 also includes a pair of tissue penetrating tips 132 and 134. Double ended surgical needle 112 is secured within the second loading unit 60 in a manner substantially identical to secure a length of double ended surgical needle 32 within first loading unit 26.

In order to protect first and second suture assemblies 30 and 108, suture retainer 110 is provided with a pair of safety covers 136 and 138 which are configured to cover upper and lower sides 18 and 20 of suture retainer 10. As noted herein above, alternatively, a length of covering material may be positioned beneath tabs 58 formed in first and second side walls 46 and 48 to protect first suture assembly 30. Likewise, while not specifically shown, a similar length of covering material may be positioned over the second tray to protect second suture assembly 108.

Referring now to FIGS. 5-8, the use of a surgical suturing apparatus such as, for example, surgical suturing apparatus 140 to remove first suture assembly 30 from within suture retainer 10 will now be described. A particularly suitable surgical suturing apparatus 140 is disclosed in U.S. Pat. No. 5,728,107 entitled "SURGICAL SUTURING APPARATUS WITH LOADING MECHANISM", the entire disclosure of which is incorporated by reference herein. Referring initially to FIG. 5, surgical suturing apparatus 140 generally includes a body portion 142 having an elongate tubular member 144 extending distally from body portion 142. A pair of needle grasping jaws, such as first and second jaws 146 and 148, is pivotally mounted on a distal end 150 of elongate tubular member 142. First and second jaws 146 and 148 are movable from an open positioned substantially spaced apart to a closed position wherein first and second jaws 146 and 148 are substantially adjacent to each other. A pair of handles 152 and 154 is provided on body portion 142 to move first and second jaws 146 and 148 between the open and closed positions. Needle holding recesses 156 and 158 are formed within first and second jaws 146 and 148, respectively, to receive and engage tissue penetrating tips 124 and 126 of surgical needle 32. A toggle lever 160 is provided to alternately secure surgical needle 32 within one of first and second jaws 146 and 148. An override switch 162 is provided to secure surgical needle 132 within needle recesses 156 and 158 when first and second jaws 146 and 148 are in a closed positioned so as to enable surgical suturing apparatus 140 to remove surgical needle 32 from first loading unit 26.

Referring now to FIG. 6, initially surgical needle 32 is supported within needle block 72 in first loading unit 26. Surgical suturing apparatus 140 is manipulated to position distal end 150 of elongate tubular member 144 within recess 76 formed in first loading unit 26. Distal end 150 is retained within first loading unit 26 by engagement with first and second tabs 84 and 86. Distal end 150 is advanced distally within first loading unit 26 until it engages abutment surface 80 formed on proximal end 78 of needle support member 68. Distal end 150 of elongate tubular member 144 is secured within first loading unit 26 by engagement with support stud 88 provided within recess 76.

Referring now to FIGS. 5 and 7, handles 152 and 154 are actuated to move first and second jaws 146 and 148 from the open to closed positions. As first and second jaws 146 and 148 are moved to the closed position, tissue penetrating tips 124 and 126 enter needle recesses 156 and 158 formed in first and second jaws 124 and 126, respectively. Operation of toggle lever 160 and override switch 162 function to secure surgical needle 32 within first and second jaws 146 and 148.

Figure 8:
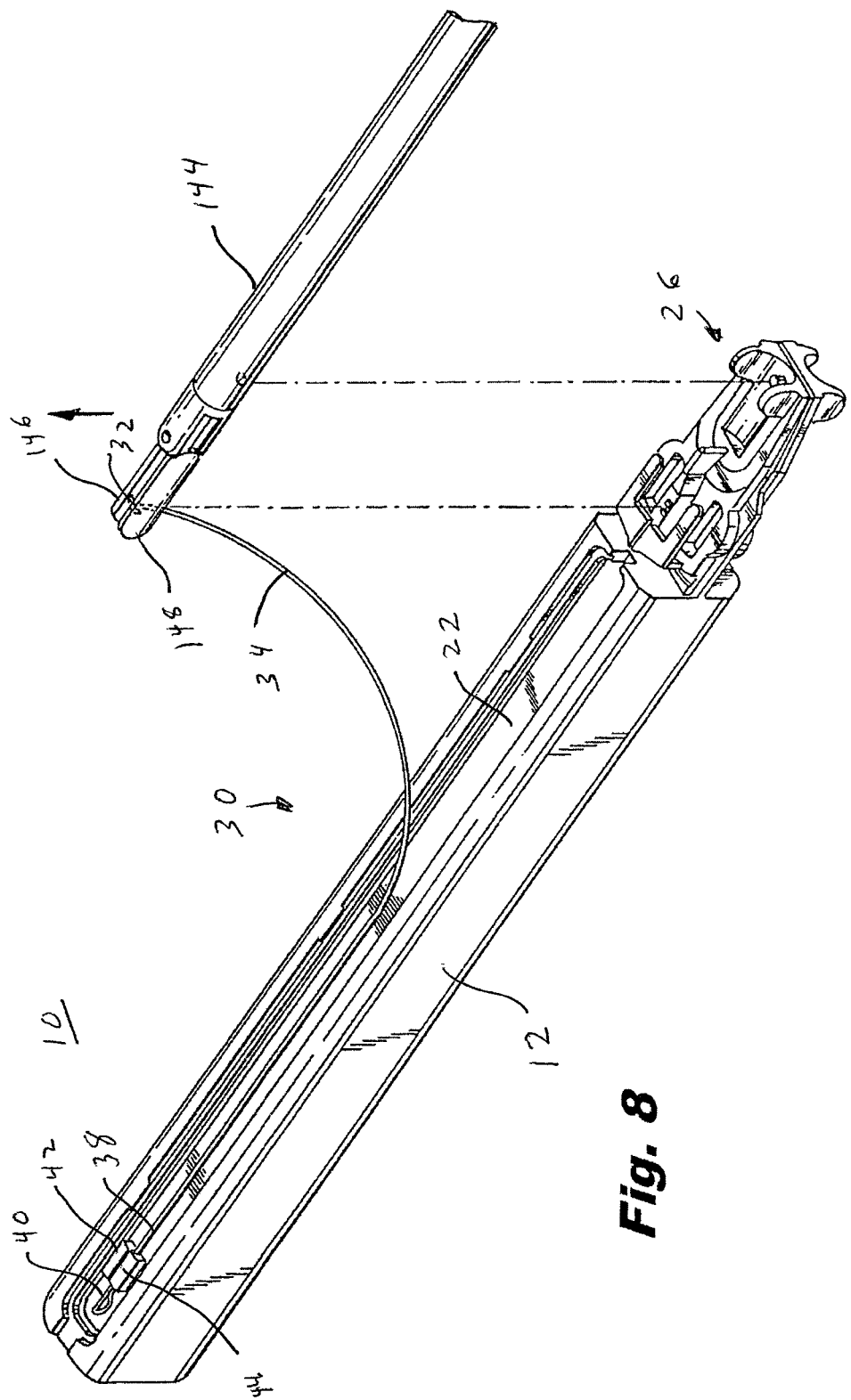
FIG. 8 is a perspective view of the surgical suturing apparatus removing the surgical needle and an associated length of suture from the knotless suture retainer.

Referring now to FIGS. 7 and 8, as shown, when first and second jaws 146 and 148 are in the closed position they may be lifted upwardly through gap 104 defined between first and second proximally extending arms 100 and 102. Additionally, length of suture material 34 is free to pass upwardly through distal gap 106 defined between proximally extending arms 100 and 102 and through notch 54 are defined in proximal wall 50 upper side 18 of elongate body portion 12. Continued lifting of elongate tubular member 144 will serve to draw length of suture material 34 out of first suture tray 22 and pull proximal end 38 of length of suture material 34 free from within center slit 44 in first retainer block 42.

Thus, suture retainer 10 provides a safe and convenient method of supplying a suture assembly, including a double ended surgical needle having a length of relatively rigid suture material attached thereto, to surgical suturing apparatus 140.

Figure 9:
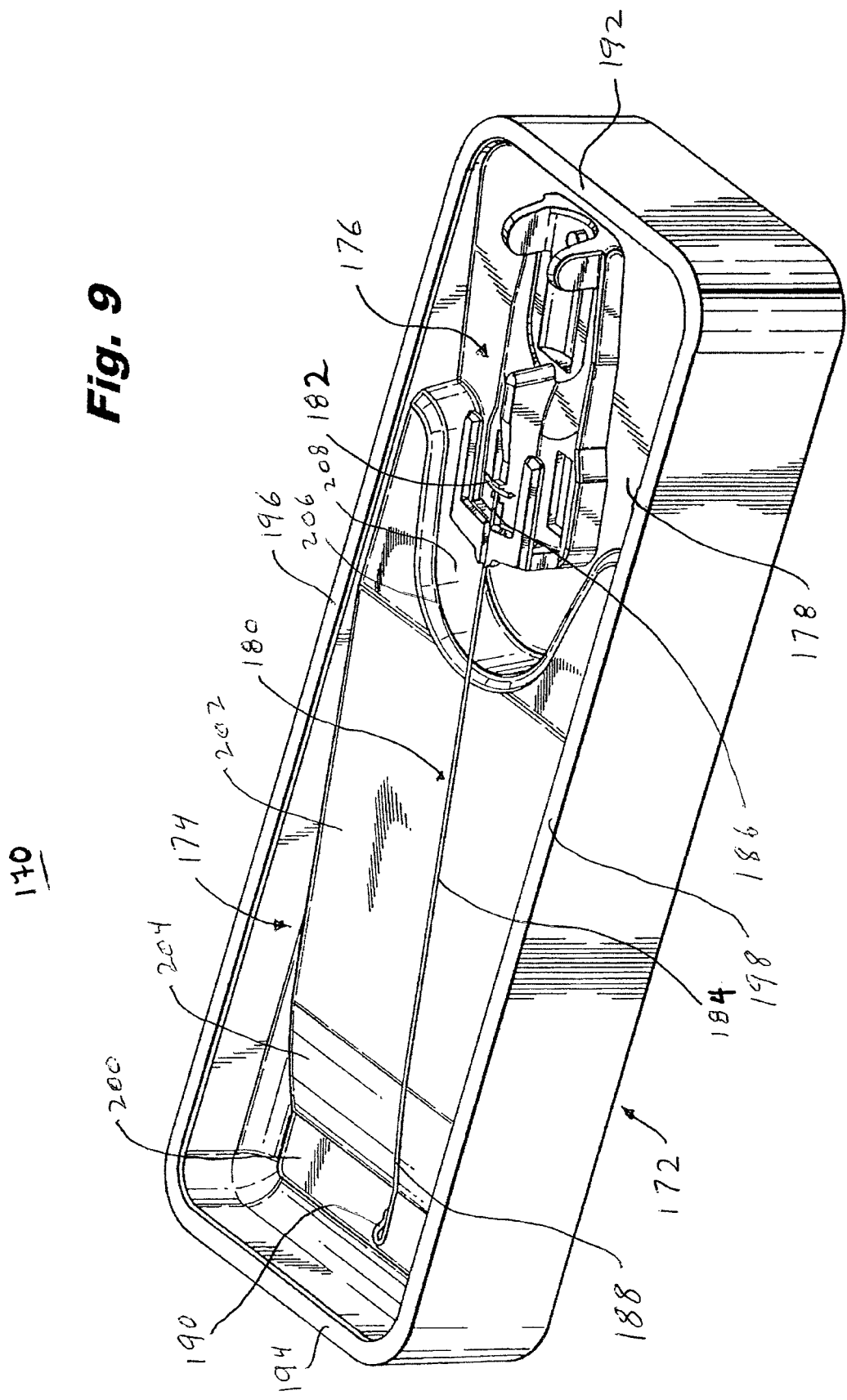
FIG. 9 is a perspective view of a second embodiment of a knotless suture retainer.

Referring now to FIGS. 9-12, and initially with regard to FIG. 9, there is disclosed an alternative embodiment of a knotless suture retainer 170. Suture retainer 170 generally includes an elongate body portion 172 defining a suture tray 174 and a loading unit 176 is positioned within a proximal tray portion 178 of suture tray 174. A suture assembly 180, similar to suture assembly 30 described herein above, is provided and includes a double ended, surgical needle 182 having a length of suture material 184 extending distally from surgical needle 182. A proximal end 186 of length of suture material 184 is affixed to double ended surgical needle 182 while a distal end 188 of length of suture material 184 terminates in a suture loop 190.

As discussed, elongate body portion 172 defines a suture tray 174. Elongate body portion 172 includes a proximal wall 192 and a distal wall 194. First and second side walls 196 and 198, respectively, extend between proximal wall 192 and distal wall 194 to define suture tray 174. Suture tray 174 includes a distal tray portion 200, a central tray portion 202 and proximal tray portion 178. Distal tray portion 200 is connected to central tray portion 202 by a generally arcuate first transition tray portion 204. Similarly, central tray portion 202 is connected to proximal tray portion 178 by a second transition tray portion 206. Second transition tray portion 206 forms a generally arcuate or U-shaped vertical wall 208 between proximal tray portion 178 and central tray portion 202. Thus, proximal tray portion 178 is partially vertically recessed relative to central tray portion 202 to contain loading unit 176 within elongate body portion 172.

Figure 10:
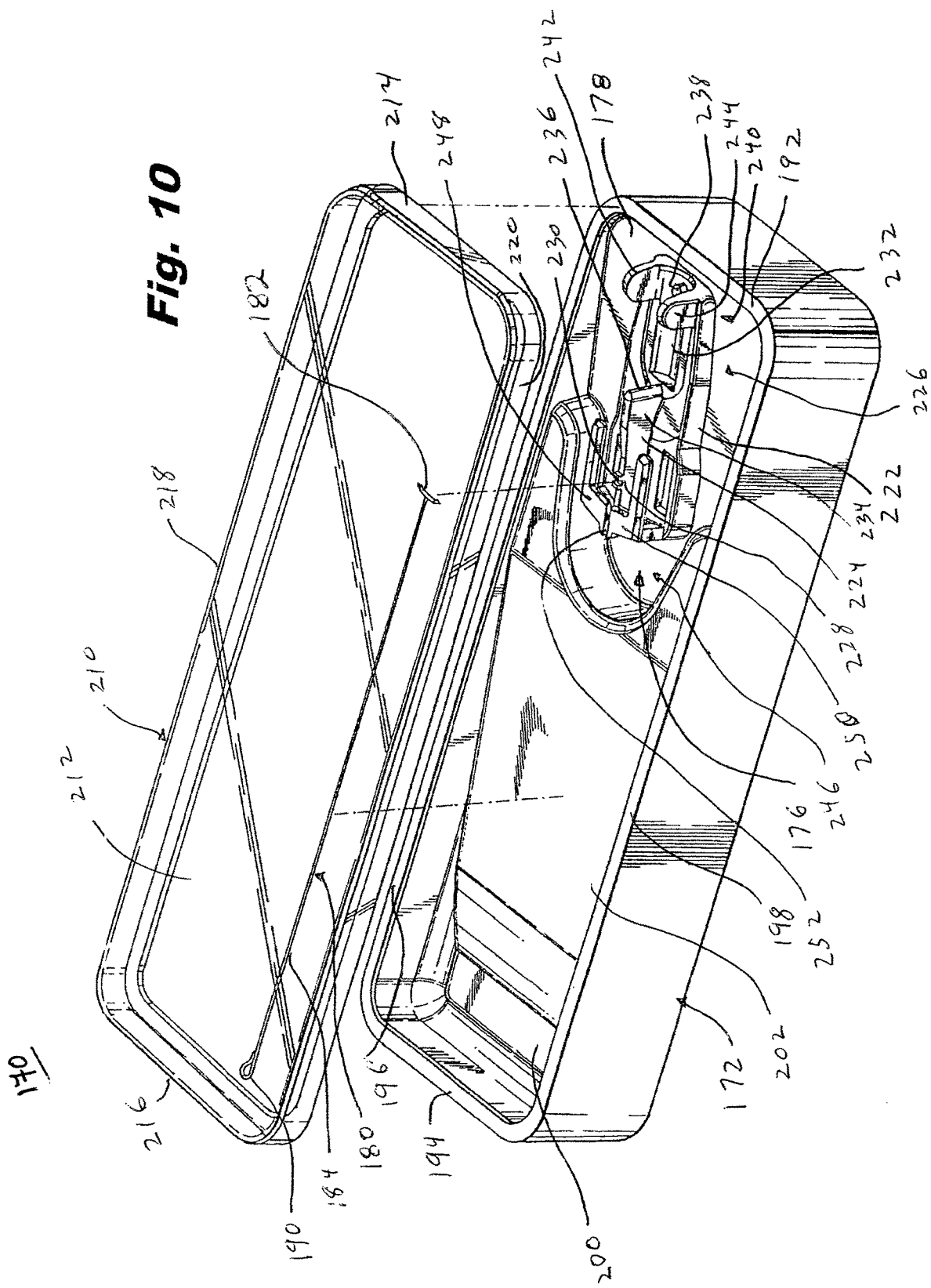
FIG. 10 is a perspective view, with parts separated, of the knotless suture retainer of FIG. 9.

Referring now to FIG. 10, suture retainer 170 additionally includes a transparent cover 210 which is provided to protect suture assembly 180 prior to use. Cover 210 includes a planner top surface 212. A proximal edge 214 and a distal edge 216 project downwardly from top surface 212. First and second side edges 218 and 220 extend between proximal edge 214 and distal edge 216 and also project downwardly from top surface 212. Proximal edge 214, distal edge 216 and first and second side edges 218 and 220 overlie proximal wall 192, distal wall 194 and first and second side walls 196 and 198 when cover 210 is positioned over elongate body portion 172.

Referring to FIGS. 10 and 11, and as noted here in above, suture retainer 170 includes a loading unit 176 which is substantially identical to loading unit 26 described herein above with regard to suture retainer 10. Specifically, loading unit 176 generally includes a base 222 having a needle support member 224 extending vertically upwardly from base 222. Base 222 may be positioned on proximal tray portion 178 or may be formed integrally therein. Apparatus receiving structure 226 is provided on base 222 for receipt of a surgical suturing apparatus. A needle block 228 is provided on needle support member 224 and includes a notch 230 (FIG. 10) for receipt and support of surgical needle 182.

Apparatus receiving structure 226 includes a recess 232 for receipt of distal end 150 of elongate tubular member 144 of surgical suturing apparatus 140 (FIG. 5) a proximal end 234 of needle support member 224 forms and abutment surface 236 in order to limit the depth of insertion of surgical suturing apparatus 140 within loading unit 176. A support stud 238 is provided within recess 232 to secure surgical suturing apparatus 140 with a loading unit 176 and a manner substantially identical to that described herein above.

Loading unit 176 additionally includes alignment structure 240 to properly position first and second jaws 146 and 148 on distal end 150 of surgical suturing apparatus 140 adjacent surgical needle 182. Alignment structure 240 includes first and second side tabs 242 and 244 which are configured to engage elongate tubular member 144. Identical to loading unit 26 described herein above, loading unit 176 includes blocking structure 246 in the form of first and second blocking members 248 and 252 prevent removal of surgical needle 182 until it has been fully grasped within first and second jaws 146 and 148 of surgical suturing apparatus 140. Additionally, as noted here in above, blocking members 248 and 252 prevent removal of surgical suturing apparatus 140 from within loading unit 176 until first and second jaws 146 and 148 have been moved to the fully closed position.

A gap 252 is defined between first and second blocking members 248 and 250 in order to allow proximal end 186 of length of suture material 184 to be lifted clear of loading unit 176.

Referring now specifically to FIG. 12, distal tray portion 200 extends perpendicularly from distal wall 194 and is substantially parallel to a bottom surface 254 of elongate body portion 172. As shown, central tray portion 202 forms and angle α with bottom surface 254 and proximal tray portion 178 forms and angle β with bottom surface 254. It should be noted that, while angles α and β are illustrated as being substantially identical, it is contemplated herein that these angles may differ so as to support suture assembly 180. A proximal end 256 of base 222 is flush with a top edge 258 of proximal wall 192. This elevates apparatus receiving structure 226, and specifically side tabs 224 (FIG. 11) and 244 above top edge 258 to allow surgical suturing apparatus 140 to be inserted into loading unit 176.

Figure 13:
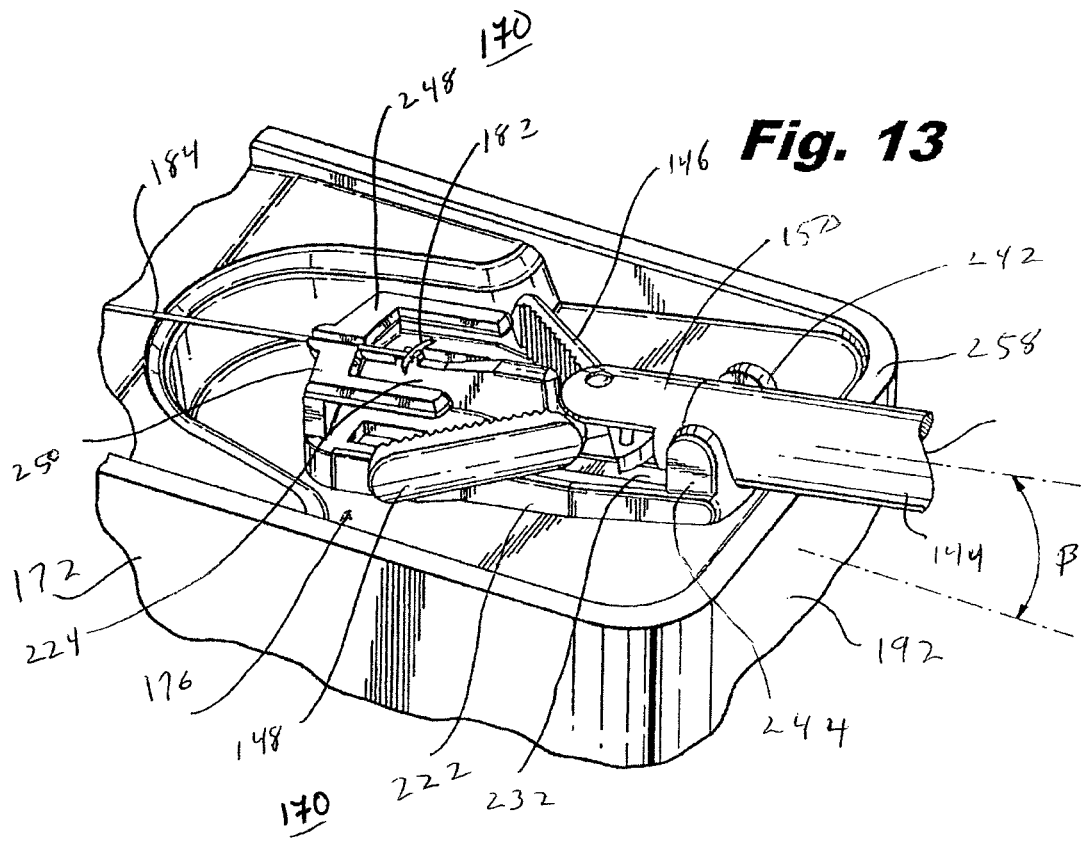
FIG. 13 is a perspective view of a surgical suturing apparatus positioned in a loading unit of the knotless suture retainer of FIG. 9.
Figure 14:
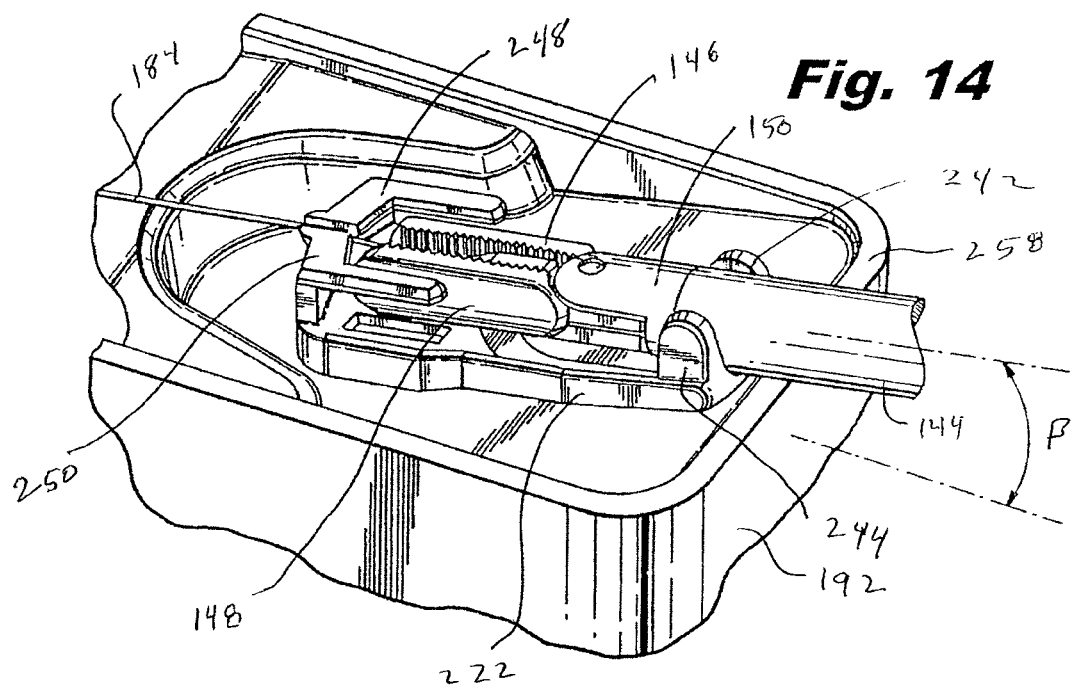
FIG. 14 is a perspective view of jaws of the surgical suturing apparatus closed about a surgical needle held in the loading unit.
Figure 15:
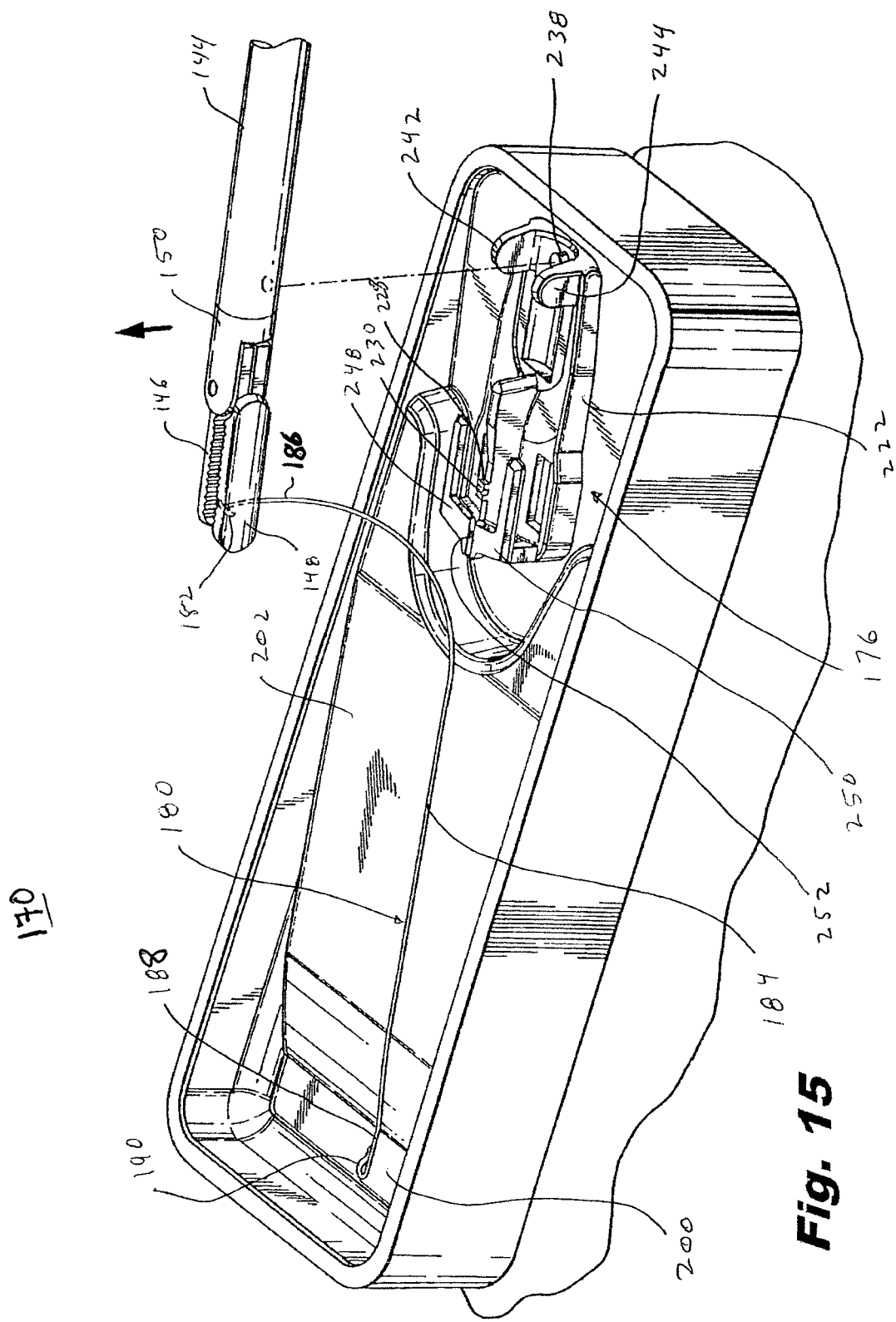
FIG. 15 is a perspective view of the surgical suturing apparatus removing the surgical needle and an associated length of suture from the knotless suture retainer of FIG. 9.

Referring now to FIGS. 13-15, and initially with regard to FIG. 13, the use of suture retainer 170 to supply suture assembly 180 to surgical suturing apparatus 140 will now be described. Surgical needle 182 is removed from loading unit 176 in a manner substantially identical to that described herein above with regard to surgical needle 32 and loading unit 26. Specifically, surgical suturing apparatus 140 is manipulated so as to advance distal end 150 within loading unit 176. As shown, since base 222 is oriented at an angle β relative to elongate body portion 172, elongate tubular member 144 of surgical suturing apparatus 140 approaches loading unit 176 a corresponding angle β. Elongate tubular member 144 is secured between tabs 242 and 244 on loading unit 176. First and second jaws 146 and 148 of surgical suturing apparatus are positioned adjacent surgical needle 182 and beneath blocking members 248 and 250.

Handles 152 and 154 of surgical suturing apparatus 140 (FIG. 5) are then manipulated to move jaws 146 and 148 from the open to the closed position passing under blocking members 248 and 250. Upon movement of the closed position, first and second jaws 146 and 148 securely grasp surgical needle 182 (FIG. 14).

Referring to FIG. 15, once surgical needle 182 has been firmly grasped and secured within first and second jaws 146 and 148, elongate tubular member 144 of surgical suturing apparatus 140 may be lifted vertically to remove elongate tubular member 144 from between tabs 242 and 244 in order to lift surgical needle 182 out of notch 230 in needle block 228. Additionally, a recess 260 formed in elongate tubular member 144 is lifted clear of support stud 238. Jaws 146 and 148 pass upwardly between blocking members 248 and 250 thereby drawing proximal end 186 of length of suture material 184 upwardly through gap 252 defined between first and second blocking members 248 and 250.

In this manner, suture assembly 180 may be removed from suture tray 174 as length of suture material 184 is lifted off of central tray portion 202 and proximal end 180, including suture loop 190, is lifted free of distal tray portion 200. Thus, suture retainer 170 provides a secure and convenient method of supplying suture assembly 182 surgical suturing apparatus 140.

Figure 16:
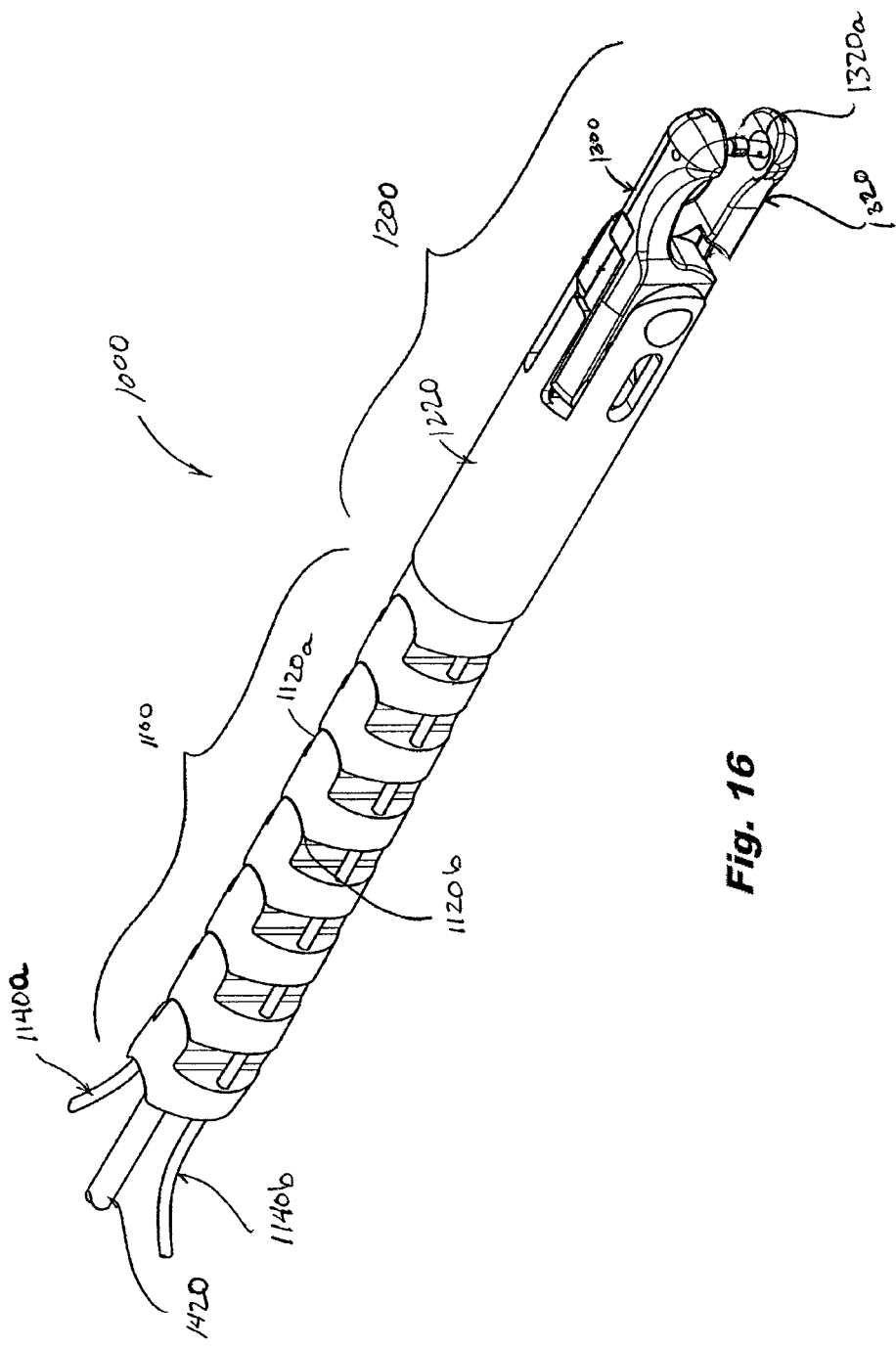
FIG. 16 is a perspective view of a distal end of an alternate embodiment of a surgical suturing apparatus for use with the knotless suture retainer.

While suture retainer 10 has been shown and described for use with surgical stapling apparatus 140, it is contemplated that suture retainer 10 may equally be used with a surgical suturing apparatus having a distal end or end effector 1000, as shown in FIG. 16.

As seen in FIG. 16, end effector 1000 includes a neck assembly 1100 supported on a distal end of a shaft extending from a handle assembly, and a tool assembly 1200 supported on a distal end of neck assembly 1100. Neck assembly 1100 includes a plurality of joints 1120 each including a distal knuckle 1120a and a proximal clevis 1120b formed therewith. Each knuckle 1120a operatively engages a clevis 1120b of an adjacent joint 1120. Each joint 1120 defines a central lumen (not shown) formed therein and a pair of opposed lumens (not shown) formed on either side of central lumen. A pair of articulation cables 1140a, 1140b slidably extend through respective lumens of joints 1120. Neck assembly 1100 enables end effector 1000 to articulate As seen in FIG. 16, tool assembly 1200 of end effector 1000 includes a jaw support member 1220, and a pair of jaws 1300, 1320 mounted for pivotable movement on jaw support member 1220. Each jaw 1300, 1320 includes a needle receiving recess 1300a, 1320a, respectively, configured to surround and hold at least a portion of a surgical needle disposed therein substantially perpendicular to tissue engaging surfaces thereof.

For a more detailed discussion of the construction and operation of end effector 1000, reference may be made to International Patent Application No. PCT/US07/21457, filed on Oct. 5, 2007, entitled "FLEXIBLE ENDOSCOPIC STITCHING DEVICES", the entire disclosure of which is incorporated by reference herein.

It will be understood that various modifications may be made to the embodiments disclosed herein. For example, the disclosed suture trays need not be planner but may present other cross-sections such as, for example, arcuate etc. Further, while the disclosed suture retainers are described with regard to a double ended surgical needle, single ended surgical needles are also contemplated as are surgical suturing apparatus capable of manipulating single ended surgical needles. Additionally, the disclosed suture retainer is may be configured to provide more than one suture assembly to a surgical suturing apparatus. Therefore, the above description should not be construed as limiting, but merely as exemplifications of particular embodiments. Those skilled in the art will envision other modifications within the scope and spirit of the claims appended hereto.

What is claimed is:

1. A suture retainer comprising:
   an elongate body portion including:
   a distal portion including a bottom surface defining a plane;
   a central portion defining a first acute angle with respect to the bottom surface, the first acute angle being fixed;
   a first transition portion interposed between the distal and central portions, the first transition portion having an arcuate profile interconnecting the distal and central portions;
   a proximal portion defining a second acute angle with respect to the bottom surface, the second acute angle being fixed; and
   a second transition portion interconnecting the central and proximal portions, the second transition portion having a wall having a U-shape; and
   a loading unit disposed in the proximal portion, the loading unit including a needle support member and a receiving structure configured to receive an elongate tubular member of a surgical suturing apparatus.

2. The suture retainer according to claim 1, wherein the first and second acute angles are identical.

3. The suture retainer according to claim 1, wherein the proximal portion defines a recess.

4. The suture retainer according to claim 1, wherein the loading unit is configured to receive the elongate tubular member of the surgical suturing apparatus at the second acute angle relative to the bottom surface.

5. The suture retainer according to claim 1, wherein the needle support member of the loading unit includes an abutment surface configured to limit axial displacement of the elongate tubular member of the surgical suturing apparatus.

6. The suture retainer according to claim 1, wherein the receiving structure includes tabs configured to receive the elongate tubular member of the surgical suturing apparatus therebetween.

7. The suture retainer according to claim 1, wherein the loading unit includes a blocking structure including first and second members defining a gap therebetween, wherein the first and second members are configured to inhibit removal of the elongate tubular member of the surgical suturing apparatus from the loading unit when jaw members of the surgical suturing apparatus are spaced part, wherein the gap is dimensioned to receive the jaw members therethrough when the jaw members are approximated to enable removal of the surgical suturing apparatus from the loading unit.

8. The suture retainer according to claim 1, further comprising a suture assembly including a suture material, a first end including a surgical needle, and a second end having a loop.

9. The suture retainer according to claim 8, wherein at least a portion of the suture material supported on the loading unit is aligned with at least a portion of the suture material disposed in the central or distal portions of the elongate body portion.

10. The suture retainer according to claim 8, wherein the needle support member of the loading unit defines a notch configured to securely receive the surgical needle of the suture assembly such that the suture assembly extends distally therefrom.

11. The suture retainer according to claim 10, wherein the suture material of the suture assembly is dimensioned such that the loop of the suture assembly is disposed in the distal portion.

12. The suture retainer according to claim 8, wherein the suture material of the suture assembly is linear along an entire length thereof.

13. The suture retainer according to claim 8, further comprising a cover configured to enclose the suture assembly disposed in the elongate body portion.

14. The suture retainer according to claim 1, wherein the loading unit is fixed against rotation relative to the central portion.

15. The suture retainer according to claim 1, wherein the receiving structure includes a support stud configured to secure the surgical suturing apparatus with the loading unit.

16. The suture retainer according to claim 1, wherein the loading unit includes a base flush with an upper surface of a proximal wall of the elongate body portion.

17. The suture retainer according to claim 16 wherein the base is integrally formed with the proximal portion of the elongate body portion.

18. The suture retainer according to claim 1, wherein the bottom surface, the distal portion, the central portion, and the proximal portion of the elongate body portion are fixed relative to each other.

* * * * *